United States Patent [19]

Johnson

[11] Patent Number: 4,758,156
[45] Date of Patent: Jul. 19, 1988

[54] TOOL FOR USE IN APPLYING FILLER MATERIAL TO AN ENDODONTICALLY PREPARED ROOT CANAL

[76] Inventor: William B. Johnson, 4254 E. 78th St., Tulsa, Okla. 74136

[21] Appl. No.: 33,254

[22] Filed: Apr. 2, 1987

[51] Int. Cl.⁴ ............................................. A61C 5/02
[52] U.S. Cl. ..................................................... 433/81
[58] Field of Search .......................... 433/81, 102, 83

[56] References Cited

U.S. PATENT DOCUMENTS

| 4,353,698 | 10/1982 | McSpadden | 433/81 |
| 4,397,634 | 10/1982 | Biggs | 433/225 |
| 4,457,710 | 7/1984 | McSpadden | 433/81 |

Primary Examiner—Robert Peshock
Attorney, Agent, or Firm—Head & Johnson

[57] ABSTRACT

A tool for use in applying filler material, such as gutta-percha or the like, to an endodontically prepared root canal of a tooth in the form of an elongated shaft of material having high biological tolerance, the shaft having a handle portion at the proximal end, the shaft being adaptable to receive filler material formed thereon formed into a conical configuration so that the shaft having the filler material thereon may be positioned in the root canal and the shaft thereafter severed by applying force to the handle portion to retain the portion of the shaft and the filler material within the root canal.

20 Claims, 3 Drawing Sheets

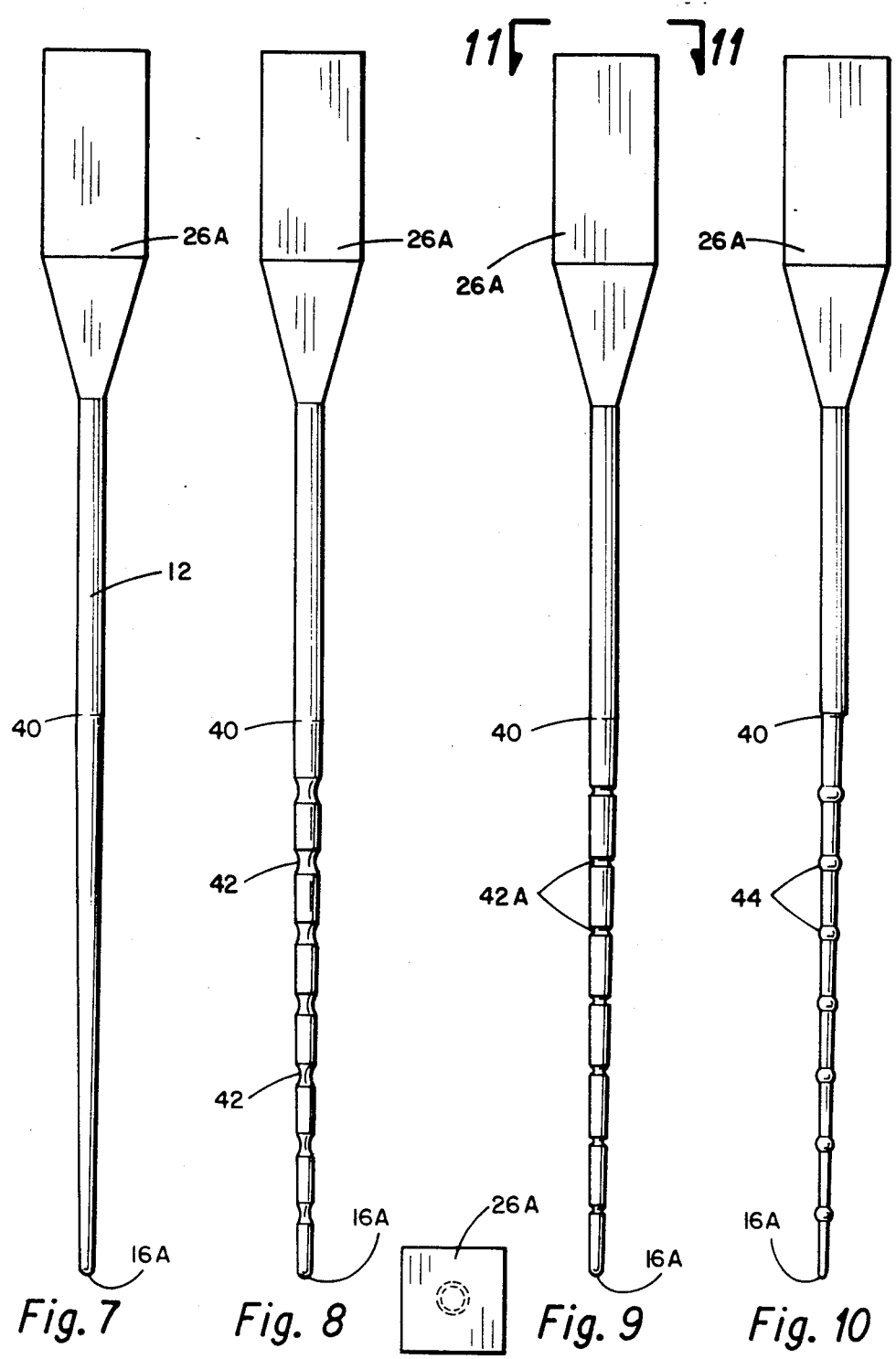

TOOL FOR USE IN APPLYING FILLER MATERIAL TO AN ENDODONTICALLY PREPARED ROOT CANAL

SUMMARY OF THE INVENTION

The conventional techniques for performing endodontic therapy on teeth are time consuming and often do not adequately ensure that the entire canal system is filled with the repair material. Experience has shown that it is not possible to remove all pulpal remnants and contaminants from a root canal with current preparation techniques. If the said pulpal remnants and contaminants are thoroughly entombed in the repair material, the endodontic therapy will be successful. If said remnants and contaminants are not thoroughly entombed, there is a high probability of failure of the endodontic therapy. Complete entombment of the remnants and contaminants requires complete obturation of the canal system. Experience has shown failure to completely obtrurate the canal system to be the primary cause of failure in endodontic therapy.

Incomplete obturation of a root canal system is primarily due to insufficient hydrostatic pressure to effect the proper flow of the filler material to the irregularities of the canal system. Canals are seldom circular in cross section. Thus, any repair material inserted into the canal must be able to compensate for the lack of circularity by flowing to the major diameter volumes. Canals will often have lateral canals and fissures that must be filled with the repair material to ensure the success of the therapy. Hydrostatic pressure must be applied to the repair material to ensure its flow into the lateral canals and fissures.

A common endodontic procedure employs silver cones used in conjunction with pastes to fill irregularities. Silver, being a highly malleable metal, will bend and adjust to the curvature of a root canal; but, since silver cones are manufactured in true circular cross section, they do not adjust to a canal that is irregular in cross section which is most often the case. The silver cones are not capable of exerting hydrostatic pressure on the sealer material, thus there is no satisfactory assurance that lateral canals and fissures are sealed.

Another common endodontic procedure employs a filler material, such as gutta-percha as the repair material. Gutta-percha is a semi-rigid material at normal room temperature. However, when it is heated, it becomes less rigid and will flow when force is applied to it. Gutta-percha, however, does not retain heat very long, thus the technique requires small amounts of the material be heated and packed into the canal in sequential manner with frequent reheating of the material in the canal. This process is slow and time consuming and also is fraught with the risk that gutta-percha deep into the canal will not be heated sufficiently by in-situ techniques and thus, will not flow properly into the irregularities of the canal.

Another common endodontic procedure is to employ a gutta-percha heating and injection device. This device is commonly referred to as a gutta-percha gun. The gun supplies the gutta-percha to the canal heated and under sufficient pressure so as to insure that the canal irregularities will be adequately filled. The problem with the gun technique is that there is no satisfactory method of insuring that the repair material will not extrude through the apex of the root and result in an impacted mass left in the gum.

It is obvious that a technique that can administer a repair material throughout the canal under sufficient hydrostatic pressure will ensure that all the lateral canals and fissures will be filled and will also ensure that all of the remnant pulpal material and contaminants will be sufficiently entombed. It is further obvious that if the technique could adequately prevent the extrusion of the repair material through the canal apex, it would be an improvement over the known techniques. It is further obvious that if the techniques could be performed in a single operation rather than in a sequential fashion there would be time and thus economic advantages of significance over the known techniques. The invention described hereunder offers these advantages.

The device of the present invention is in the form of a rigid carrier member coated with gutta-percha or similar filler material. The carrier member is a tapered, slender rod. The carrier member may be constructed of any material which is of sufficient rigidity and non-toxic when left in the root canal. One material that has been employed successfully is stainless steel. A plastic or aluminum carrier member also works successfully.

The carrier member incorporates a matte finish, or radial ribbing or helixes to provide adhesion surfaces for the gutta-percha and to serve as a mechanical piston to assist in forcing the gutta-percha into the canal.

In one embodiment the tip of the carrier member that is intended for the apex end of the canal incorporates a flat surface which is pointed at the extremity. The carrier member can thus be forced into the canal at a sufficient depth into the taper which then prevents the carrier member from being able to rotate in the canal. A shaft of the carrier member has an area of lesser diameter than the normal diameter. This point of minor diameter or reduced torque resistance area is designed to fail when a certain level of torque is applied to the handle of the carrier member. The flat on the extremity of the carrier member prevents rotation of the carrier member, thus the member will fail when a torque is applied to the handle. The reduced torque resistance area is located at a specific point on the carrier member at the desired level in the canal. The portion of the carrier member shaft above the reduced torque resistance area is of constant cross section (i.e. not ribbed) to facilitate removal of the member through the semi-rigid gutta-percha without pulling said gutta-percha out of the canal.

A disc-shaped washer is incorporated on the shaft of the carrier member and serves to act as a stopping plug at the coronal opening of the canal and thus to prevent viscous flow of the gutta-percha out of the said canal during the insertion process.

The gutta-percha is molded to the carrier member in a tapered or conically-shaped manner so as to facilitate the introduction into the typical canal taper with sufficient material to ensure complete filling of the said canal and thereby complete obturation of the canal.

The devices may be manufactured in a variety of sizes to correspond to standard endodontic files.

In using the tool of this invention the root canal is first prepared in the standard manner by broaching with endodontic files. The final file used in the apex preparation determines the proper gutta-percha device. A carrier member of proper size is prepared with gutta-percha and the gutta-percha is heated over to the point at which the surface is glossy. The heated apparatus is then inserted into the root canal with firm apical force. The handle portion of the carrier member is then rotated while maintaining the apical force until torsional failure occurs.

The shank of the carrier member is then removed while holding the stopping plug or washer against the tooth and the remainder of the endodontic therapy is completed using conventional procedures.

For more information as to background material relating to the present invention reference may be had to pages 184 through 188 of the *Journal of Endodontics*, Volume 4, No. 6, June 1978 which describes a new gutta-percha technique in which the gutta-percha is formed around an endodontic file.

A better understanding of the invention will be had by reference to the following description and claims, taken in conjunction with attached drawings.

DESCRIPTION OF THE DRAWINGS

As shown in FIG. 2 apparatus is ready for use in filling an endodontically prepared root canal.

FIG. 7 is an elevational view of an alternate embodiment of the tool of FIG. 1 in which the shaft of the tool has a matte surface finish.

FIG. 8 is an elevational view of an additional alternate embodiment substantially that of FIG. 7 but wherein the shaft includes spaced circumferential indentations.

FIG. 9 is an elevational view of an embodiment as in FIGS. 7 and 8 wherein the shaft includes spaced indentations which are relatively narrow compared to the indentations of FIG. 8.

FIG. 10 is an elevational view of a still different embodiment including spaced enlarged diameter portions on the shaft.

FIG. 11 is an end view taken along the line 11-11 of FIG. 9.

DETAILED DESCRIPTION OF THE PREFERRED EMBODIMENT

Figure 1:
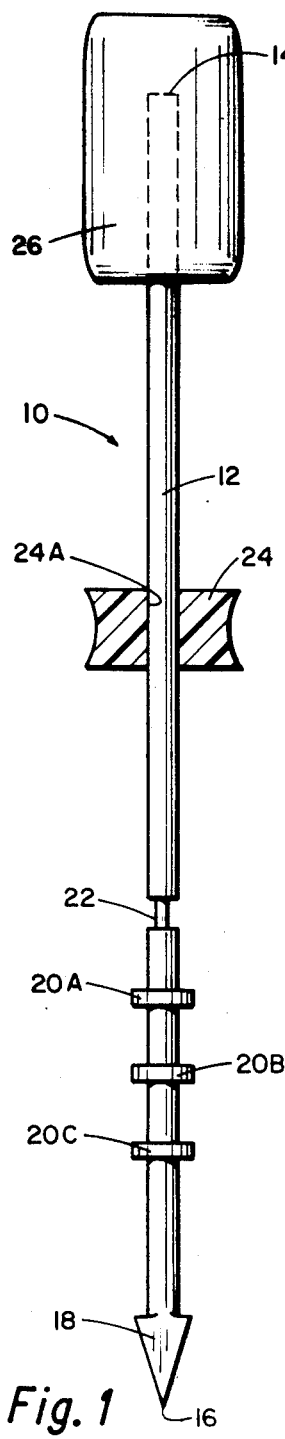
FIG. 1 is an enlarged elevational view of the tool, or carrier member of the present invention. The tool includes a slidable stopper or washer which is shown in cross-section.

Referring to the drawings, and first to FIG. 1, the tool which is a carrier member, is generally indicated by numeral 10 and is formed of an elongated shaft 12 having a proximal end 14 and distal end 16. While the shaft may be of a variety of cross-sectional configurations the preferred and simplest shape is that of a circular cross-sectional configuration as illustrated. At the proximal ends 16 the shaft is flattened or flared at 18 into a non-circular cross-sectional configuration so that when the shaft is positioned in a root canal of a tooth, as will be hereinafter more specifically described, the flared end portion 18 resists rotation of the shaft. Integrally formed on the shaft are a plurality (three being shown) of spaced apart enlarged cross-sectional dimensioned portions 20A through 20C. When the shaft is circular cross-sectional as preferred, the enlarged diameter portion 20A, 20B and 20C are also preferably an enlarged circular cross-sectional configuration. Instead of spaced apart enlarged cross-sectional portions, an alternate arrangement, not illustrated, includes integral spiraled portions extending from the shaft body.

Positioned between the enlarged diameter portion 20A, and the proximal end 14 is a reduced torque resistance area 22. This is in the form, as shown, of a groove formed around the shaft. Between groove 22 and the proximal end 14 is a sliding stopper or washer 24 having an opening 24A therein which slidably receives shaft 12.

Affixed to the shaft at the proximal end 14 is a handle portion 26.

Handle 26 is of a diameter larger than that of a shaft 12 and may be integral with the shaft or is secured to the shaft and made of a material such as plastic.

Figure 2:
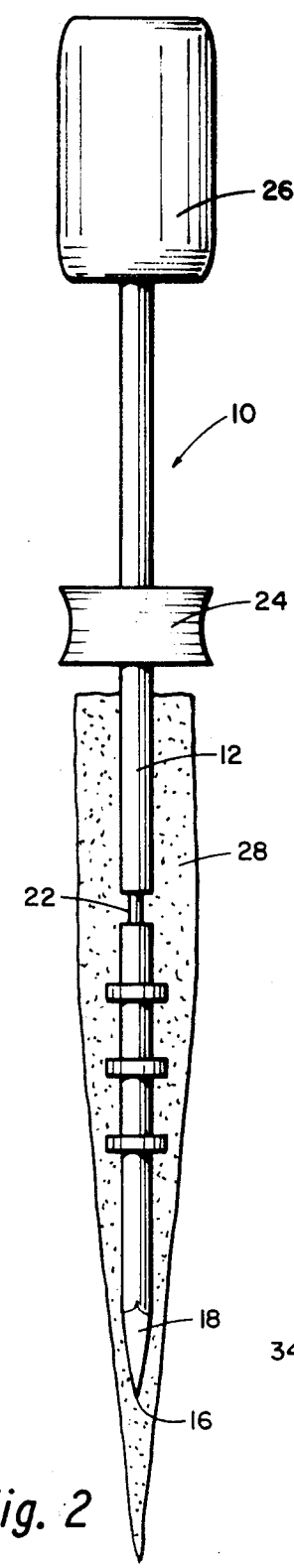
FIG. 2 is an elevational view as in FIG. 1 showing the lower portion of the tool as encapsulated in a conically-shaped quantity of filler material, such as gutta-percha.

FIG. 2 shows the appliance ready for use in inserting a filler material, such as gutta-percha into the root canal of an endodontically prepared tooth. FIG. 2 shows, in cross-section, filler material 28 formed on the tool 10. The filler material 28 may be such as gutta-percha which can be formed by hand onto tool 10. After forming, the gutta-percha may be warmed in a flame to the proper stage.

Figure 3:
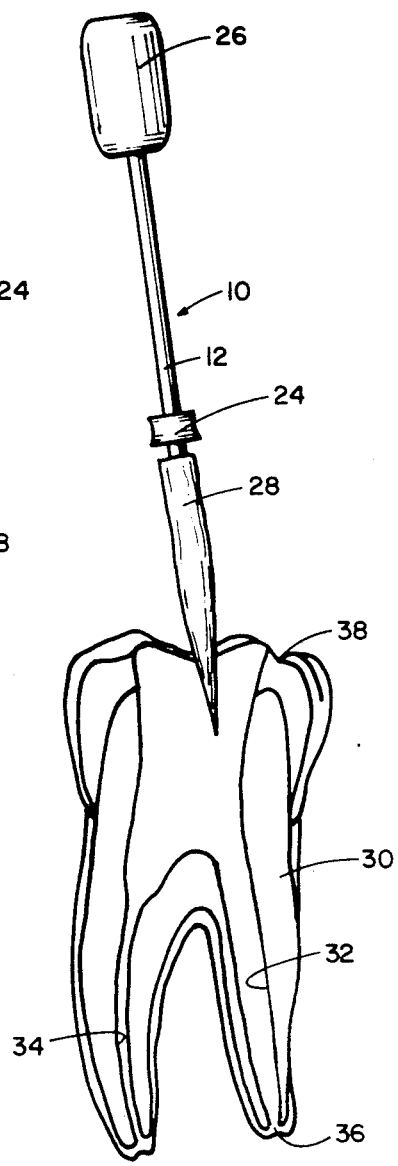
FIG. 3 shows a tooth in cross-section with the root canal having been endodontically prepared and showing the appliance of this invention, in reduced scale, as being employed to apply filler material to one of the endodontically prepared roots.

FIG. 3 shows a tooth 30 having root canals 32 and 34 therein. A canal 32 has been endodontically prepared in the standard technique such as by the use of files to remove the root pulp and to prepare, as well as possible, a clean canal. The appliance formed of tool 10 with the filler material 28 molded thereon is ready for use for filling the root canal 32. The apex of the root canal is indicated at 36 with the tooth crown or coronal portion being indicated by numeral 38.

Figure 6:
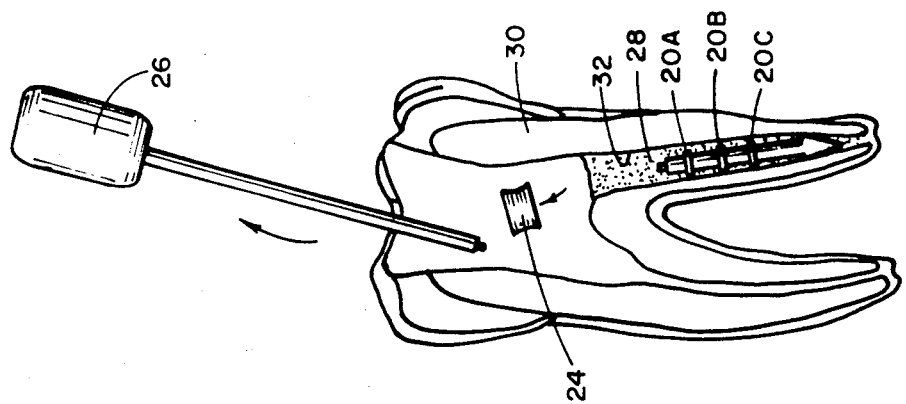
FIG. 6 shows the removal of the proximal portion of the tool with the distal portion being retained in the root canal with the filler material.
Figure 5:
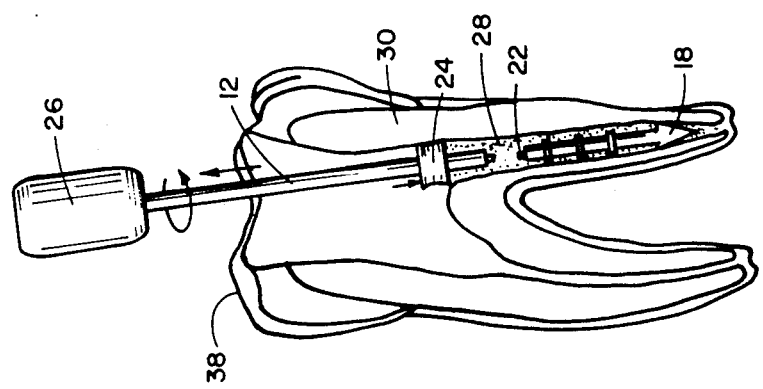
FIG. 5 shows the next step in a sequence of applying filler material to the root canal wherein the tool has been rotated to sever the proximal portion form the distal portion.
Figure 4:
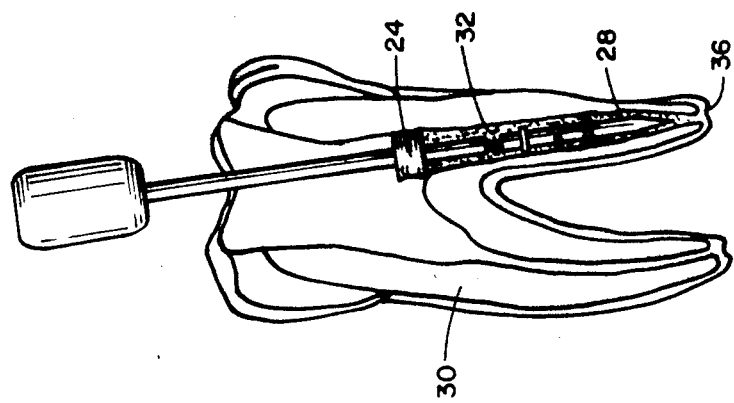
FIG. 4 is a cross-sectional view of the tooth as in FIG. 3 showing the appliance inserted into the root canal.

FIGS. 4 through 6 show the continuation of the step of filling root canal 32. FIG. 4 shows the appliance inserted into the canal 32. The filler material 28 is forced by the insertion of the appliance to fill the canal to the apical area 36 of the tooth. After full insertion of the appliance as shown in FIG. 4, rotational torque is applied to handle 26, severing the shaft at the reduced torque resistance area 22 as shown in FIG. 5. This is possible since the flared distal end 18 of the shaft resists rotation relative to tooth 30.

After the shaft has been severed into two portions, the proximal portion is withdrawn. The sliding washer 24 is used to retain the filling material 28 in the canal by holding the washer downwardly as the proximal end portion of the shaft 12 is withdrawn.

FIG. 6 shows the proximal portion of the tool being withdrawn. Washer 24 is then removed, leaving the distal portion of the shaft in place within the root canal 32. The root canal 32 can be more completely filled by applying additional filler material and by applying mechanical or hydraulic pressure to the filler material to force it into the root canal. The coronal area of the tooth can be filled in the usual way.

The depiction of the tooth 30 in FIGS. 3 through 6 is merely exemplary as teeth are individualistic and the drawings are intended to exemplify the steps involved rather than to accurately pictorially represent the appearance of the tooth or root canal therein.

The invention, thus, provides an unique and very effective way of conveying filler material, such as gutta-percha, into an endodontically prepared root canal. The prior art teaches the use of a file as a carrier of filler material, however, this known method, while functioning successfully for its intended purpose, nevertheless has limitations and problems which are overcome by the present invention.

FIGS. 7 through 11 show a family of alternate embodiments of the invention preferably formed of plastic material. The shaft 12 is of elongated tapered shape in which the distal end 16 is slightly rounded. The handle 26A is integrally formed with the shaft and, as indicated in FIG. 11, may be of non-circular cross-section, such as square as shown. Obviously, the handle may be also of hexagonal or other shapes which permits the tool to be manipulated by the endodontist.

The external surface of the shaft 12 of FIG. 7 is preferably formed with a matte finish so that filler material formed thereon, such as in FIG. 2, will be secured to the shaft for insertion into an endodontically prepared root canal. While a sliding washer is not shown in the embodiments of FIGS. 7 through 10 it is apparent that a washer can be utilized in the same way as illustrated in FIGS. 1 through 6.

The embodiment of FIGS. 7 through 10 does not include a flared end as with the embodiment of FIGS. 1 and 2, however, the lower portion of the shaft can be severed after insertion into a root canal by the provision of cuts 40 formed in the shaft. The cuts 40 are equivalent to the reduced diameter portion 22 of FIGS. 1 and 2 and provide a stress point. After the shaft is inserted into a root canal, the lower portion may be separated from the upper portion by moving the upper portion back and forth relative to the tooth in which the lower portion is positioned to break the shaft at cut 40.

FIGS. 8 and 9 show the embodiment of FIG. 7 but with spaced apart, reduced diameter recesses 42 therein. In FIG. 8 the recesses 42 are rather wide with a curved circumferential bottom surface whereas in FIG. 9 the recesses 42A are much narrower. This illustrates that the shape, size and spacing of the recesses may vary.

FIG. 10 shows an embodiment including integral enlarged diameter portions 44. These portions are semicircular in external configuration as compared with the cylindrical configurations of the enlarged diameter portions 20A through 20C as shown in FIGS. 1 and 2. The enlarged diameter portions 44 serve to help retain filler material on the shaft while it is being inserted into a root canal.

The alternate embodiments of FIGS. 7 through 10 illustrate the fact that the tool may take a variety of configurations, each of which is within the purview of the invention and each of which serves the function of permitting more ready and effective insertion of filler material into an endodontically prepared root canal.

The claims in the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A tool for use in applying filler material such as gutta-percha or the like, to an endodontically prepared root canal of a tooth, the canal extending from the tooth coronal area to the root apex, comprising:
   an elongated shaft of material having high biological tolerance, having a distal end and a proximal end and of length such that the distal end is positionable adjacent the apical area when the tool is inserted into a root canal, the shaft distal end being configured to resist rotation relative to a tooth as the shaft is forced into a root canal, the shaft having a reduced torque resistance area spaced from said distal end and positioned below the coronal area of a tooth when the shaft is positioned in a root canal, and the shaft having integral spaced apart enlarged dimensioned cross-sectional portions thereon positioned between said distal end and said reduced torque resistance area; and
   a handle portion at said shaft proximal end, the distal portion of said shaft including said enlarged dimensional cross-sectional portions being adaptable to receive filler material formed thereon whereby the shaft having filler material thereon may be inserted into an endodontically prepared root canal and the proximal portion severed from the distal portion by the application of rotational torque to the proximal end to thereby retain the distal portion and filler material within the root canal.

2. A tool for use in applying filler material according to claim 1 wherein said elongated shaft is generally circular in cross-section and said integral enlarged dimensioned cross-sectional portions are in the form of a plurality of spaced apart integral circular discs.

3. A tool for use in applying filler material according to claim 1 wherein said handle portion is in the form of an enlarged diameter cylindrical handle member affixed to said shaft at said proximal end thereof.

4. A tool for use in applying filler material according to claim 3 wherein said handle member is made of a material different than said shaft.

5. A tool for use in applying filler material according to claim 1 wherein said shaft distal end is flared into a non-circular shape providing said configuration to resist rotation relative to a tooth as the shaft is forced into a root canal.

6. A tool for use in applying filler material according to claim 1, including:
   a stopper washer slideably received on said shaft between said handle portion and said reduced torque resisting area.

7. An appliance for positioning filler material, such as gutta-percha or the like, into an endodontically prepared root canal extending from the root coronal area to the root apex, comprising:

an elongated shaft of material having high biological tolerance, having a distal end and a proximal end and of length such that the distal end is positionable adjacent the apical area when the tool is inserted into a root canal, the shaft distal end being configured to resist rotation relative to a tooth as the shaft is forced into a root canal, the shaft having a reduced torque resistance area spaced from said distal end and positioned below the coronal area of a tooth when the shaft is positioned in a root canal, and the shaft having integral spaced apart enlarged dimensioned cross-sectional portions thereon positioned between said distal end and said reduced torque resistance area;

a handle means at said shaft proximal end; and filler material formed on said shaft encompasing said distal end and said enlarged dimensional cross-sectional portions and encompasing said reduced torque resisting area, the filler material being conically-shaped, the apex thereof extending beyond said shaft distal end, whereby the shaft having said filler material thereon may be inserted into an endodontically prepared root canal and the proximal portion severed from the distal portion by the application of rotational torque to the proximal end to thereby retain the distal portion and filler material within the root canal.

8. An appliance according to claim 7 wherein said elongated shaft is of generally circular cross-section and said integral enlarged dimensioned cross-sectional portions are in the form of a plurality of spaced apart integral circular discs.

9. An appliance according to claim 7 wherein said handle means is in the form of an enlarged diameter cylindrical handle member affixed to said shaft at said proximal end thereof.

10. An appliance according to claim 9 wherein said handle member is made of a material different than said shaft.

11. An appliance according to claim 7 wherein said shaft distal end is flared into a non-circular configuration providing said configuration to resist rotation relative to a tooth as the shaft is forced into a root canal.

12. An appliance according to claim 7 including:

a stopper washer slideably received on said shaft between said handle portion and said filler material formed on said shaft.

13. A tool for use in applying filler material such as gutta-percha or the like, to an endodontically prepared root canal of a tooth, the canal extending from the tooth coronal area to the root apex, comprising:

an elongated shaft of material having high biological tolerance, having a distal end and a proximal end and of length such that the distal end is positionable adjacent the apical area when the tool is inserted into a root canal, and the shaft having an integral surface configuration adaptable to retain filler material thereon; and a handle portion of said shaft proximal end, the distal portion of said shaft adaptable to receive filler material formed thereon being insertable into an endodontically prepared root canal and the proximal portion being severable from the distal portion to thereby retain the distal portion and filler material within the root canal.

14. A tool for use in applying filler material according to claim 13 wherein said elongated shaft is generally circular in cross-section.

15. A tool for use in applying filler material according to claim 1 wherein said handle portion is in the form of an enlarged non-circular, integral handle member formed on said shaft at said proximal end thereof.

16. A tool according to claim 13 wherein said shaft integral surface configuration is in the form of a matte finish.

17. A tool according to claim 13 wherein said elongated shaft is generally circular in cross-section and includes integral, spaced apart, enlarged diameter portions.

18. A tool according to claim 13 wherein said elongated shaft is generally circular in cross-section and includes integral, spaced apart, reduced diameter portions.

19. A tool according to claim 15 wherein said handle portion is enlarged dimensionally compared to said shaft and is of square cross-section configuration.

20. A tool according to claim 13 wherein said shaft has a cut therein between said distal and proximal ends, the cut, forming a point of weakness whereby the lower portion of the shaft may be broken from the handle portion.

* * * * *

UNITED STATES PATENT AND TRADEMARK OFFICE
CERTIFICATE OF CORRECTION

PATENT NO. : 4,758,156

DATED : July 19, 1988

INVENTOR(S) : Johnson

It is certified that error appears in the above-identified patent and that said Letters Patent is hereby corrected as shown below:

Column 3, line 39, change "form" to --from--.
Column 4, line 1, change "proximal" to --distal--.
Column 7, line 17, change "encompasing" to --encompassing--;
Column 7, line 19, change "encompasing" to --encompassing--.

Signed and Sealed this

Eighteenth Day of February, 1992

Attest:

HARRY F. MANBECK, JR.

*Attesting Officer*   Commissioner of Patents and Trademarks

US004758156C1

(12) REEXAMINATION CERTIFICATE (4665th)
United States Patent
Johnson

(10) Number: US 4,758,156 C1
(45) Certificate Issued: Nov. 5, 2002

(54) TOOL FOR USE IN APPLYING FILLER MATERIAL TO AN ENDODONTICALLY PREPARED ROOT CANAL

(75) Inventor: William B. Johnson, Tulsa, OK (US)

(73) Assignee: Dentsply International Inc., York, PA (US)

Reexamination Request:
No. 90/005,904, Jan. 4, 2001

Reexamination Certificate for:
Patent No.: 4,758,156
Issued: Jul. 19, 1988
Appl. No.: 07/033,254
Filed: Apr. 2, 1987

Certificate of Correction issued Feb. 18, 1992.

(21) Appl. No.: 07/033,254

(51) Int. Cl.$^7$ ................................................ A61C 5/02
(52) U.S. Cl. ...................................................... 433/81
(58) Field of Search ............................. 433/81, 83, 102

(56) References Cited

U.S. PATENT DOCUMENTS

| | | | |
|---|---|---|---|
| 1,463,963 A | 8/1923 | Miller | 433/224 |
| 1,469,992 A | 10/1923 | Card | 433/81 |
| 3,919,774 A | 11/1975 | Fishman | 433/224 |
| 4,190,958 A | 3/1980 | Martin et al. | 433/102 |
| 4,353,698 A * | 10/1982 | McSpadden | 433/81 |
| 4,362,508 A | 12/1982 | Söderström | 433/81 |
| 4,380,433 A | 4/1983 | Ellman et al. | 433/87 |
| 4,397,634 A * | 8/1983 | Biggs | 433/225 |
| 4,439,154 A | 3/1984 | Mayclia | 433/229 |
| 4,457,710 A * | 7/1984 | McSpadden | 433/81 |
| 4,475,370 A | 10/1984 | Stark et al. | 75/53 |
| 4,480,996 A | 11/1984 | Crovatto | 433/164 |
| 4,681,545 A | 7/1987 | Lapcevic | 433/224 |

FOREIGN PATENT DOCUMENTS

| | | |
|---|---|---|
| CA | 1 220 369 | 4/1987 |
| CH | 513 640 | 10/1971 |
| DE | 27 24 516 A1 | 4/1978 |
| FR | 2163953 | 7/1973 |

OTHER PUBLICATIONS

Sampeck, "The Stainless Steel Endodontic File—Its Use In Obturation Of Difficult Root Canals," Dissertation, University of Michigan, Jun. 1961.

Ingle, *Endodontics*, 3$^{rd}$ Ed., 1985, Chapters 3 and 4.

Johnson, "A New Gutta–Percha Technique", Journal of Endodontics, vol. 4, No. 6, Jun. 1978, pp. 184–188.

Negm, "Filling Root Canals With Silver–Percha Cones: A Clinical Study," Oral Surg. Jan. 1983, pp. 82–85.

Negm, "A Newly Designed Root Canal Filling Material", British Dental Journal, 1980, 148, 9, pp. 9–11.

Palmer et al., "A Study of the Tissue Reaction to Silver Cones and Ti–6A1–4V in the Rhesus Monkey", Journal of Endodontics, vol. 5, No. 4, Apr. 1979. pp. 116–120.

Sanders and Dooley, "A Comparative Evaluation of Polycarboxylate Cement as a Root–Canal Sealer Utilizing Roughened and Nonroughened Silver Points", Oral Surg. Apr. 1974, pp. 629–640.

Cohen et al., "Pathways of the Pulp," 2$^{nd}$ Ed., 1980, pp. 339, 361–362.

\* cited by examiner

*Primary Examiner*—John J. Wilson

(57) ABSTRACT

A tool for use in applying filler material, such as gutta-percha or the like, to an endodontically prepared root canal of a tooth in the form of an elongated shaft of material having high biological tolerance, the shaft having a handle portion at the proximal end, the shaft being adaptable to receive filler material formed thereon formed into a conical configuration so that the shaft having the filler material thereon may be positioned in the root canal and the shaft thereafter severed by applying force to the handle portion to retain the portion of the shaft and the filler material within the root canal.

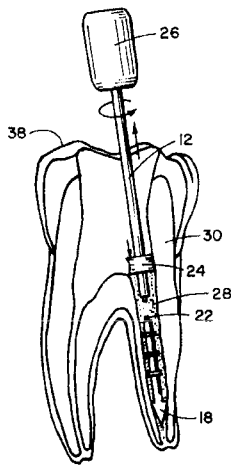

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–12, 15 and 19 is confirmed.

Claim 16 is cancelled.

Claim 13 is determined to be patentable as amended.

Claims 14, 17, 18 and 20, dependent on an amended claim, are determined to be patentable.

New claims 21–23 are added and determined to be patentable.

13. A tool [for use in applying] *in combination with a* filler material such as gutta-percha or the like[.] *for applying said filler material* to an endodontically prepared root canal of a tooth, the canal extending from the tooth coronal area to the root apex, comprising:

an elongated shaft of material having high biological tolerance, having a distal end and a proximal end and of length such that the distal end is positionable adjacent the apical area when the tool is inserted into a root canal[, and];

*said filler material molded onto at least a distal portion of said shaft adjacent said distal end, said filler material not flowable at room temperature but becoming flowable in the heated state,* the shaft having an integral surface configuration [adaptable] *adapted* to retain *said* filler material thereon, *said distal portion of said shaft on which said filler material is molded is made from a plastic material, a matte finish being formed on the surface of said plastic material, said matte finish forming adhesion surfaces that retain said molded filler material onto said distal portion of said shaft;* and a handle portion of said shaft proximal end, the distal portion of said shaft [adaptable to receive] *having* filler material [formed] *molded* thereon being insertable into an endodontically prepared root canal and the proximal portion being severable from the distal portion to thereby retain the distal portion and filler material within the root canal.

*21. A tool according to claim 13 wherein said filler material is gutta-percha that has been molded on said distal portion of said shaft.*

*22. A tool according to claim 13 wherein said shaft has a maximum diameter, and wherein said handle is of a diameter larger than said maximum diameter of said shaft.*

*23. A tool according to claim 13 wherein said handle is made from a plastic material.*

\* \* \* \* \*